US009033962B2

(12) United States Patent
Cooper et al.

(10) Patent No.: US 9,033,962 B2
(45) Date of Patent: May 19, 2015

(54) PHOTODYNAMIC THERAPY INCLUDING LIGHT PRETREATMENT

(75) Inventors: Kevin D. Cooper, Moreland Hills, OH (US); Elma D. Baron, Concord, OH (US)

(73) Assignee: Case Western Reserve University, Cleveland, OH (US)

(*) Notice: Subject to any disclaimer, the term of this patent is extended or adjusted under 35 U.S.C. 154(b) by 59 days.

(21) Appl. No.: 13/233,616

(22) Filed: Sep. 15, 2011

(65) Prior Publication Data
US 2012/0071810 A1    Mar. 22, 2012

Related U.S. Application Data

(60) Provisional application No. 61/383,390, filed on Sep. 16, 2010, provisional application No. 61/383,365, filed on Sep. 16, 2010.

(51) Int. Cl.
*A61N 5/06* (2006.01)
*A61B 18/00* (2006.01)

(52) U.S. Cl.
CPC ............ *A61N 5/062* (2013.01); *A61N 5/0616* (2013.01); *A61N 2005/0627* (2013.01); *A61N 5/0624* (2013.01); *A61B 2018/00642* (2013.01); *A61B 2018/00791* (2013.01); *A61N 2005/0629* (2013.01); *A61N 2005/0645* (2013.01); *A61N 2005/0652* (2013.01); *A61N 2005/0663* (2013.01)

(58) Field of Classification Search
USPC .................................... 606/2–19; 607/88–94
See application file for complete search history.

(56) References Cited

U.S. PATENT DOCUMENTS

| | | | | |
|---|---|---|---|---|
| 6,676,655 B2 * | 1/2004 | McDaniel | ............... | 606/9 |
| 6,887,260 B1 * | 5/2005 | McDaniel | ............... | 607/88 |
| 7,090,691 B2 * | 8/2006 | Simkin et al. | ............... | 607/88 |
| 2005/0004510 A1 * | 1/2005 | Chen | ............... | 604/20 |
| 2006/0231107 A1 * | 10/2006 | Glickman et al. | ............... | 128/898 |
| 2009/0156552 A1 | 6/2009 | Cooper et al. | | |
| 2010/0240609 A1 | 9/2010 | Guo et al. | | |

OTHER PUBLICATIONS

Maurin, Michael B., et al., "The Physicochemical Background: Fundamentals of Ionic Equilibria," Handbook of Pharmaceutical Salts; Chapter 1; pp. 9-18 (2002).

(Continued)

*Primary Examiner* — Aaron Roane
(74) *Attorney, Agent, or Firm* — Tarolli, Sundheim, Covell & Tummino LLP

(57) ABSTRACT

A method of photodynamic therapy is described that includes administering a therapeutically effective amount of a photosensitizer to an area of tissue such as the skin of a subject, delivering a first photoirradiation with light having a wavelength suitable to activate the photosensitizer to the area of skin, allowing a sufficient interval of time to pass for an effective amount of the photosensitizer to penetrate the tissue, and then delivering a second photoirradiation with light having a wavelength suitable to activate the photosensitizer to provide a therapeutic effect. Use of multiple photoirradiations increases the speed with which the photosensitizer can penetrate the tissue to reach the area where the source of the disease is present.

16 Claims, 5 Drawing Sheets

(56) References Cited

OTHER PUBLICATIONS

Baron, Elma, D., et al. "Silicon Phthalocyanine (Pc4) Photodynamic Therapy in a Safe Modality for Cutaneous Neoplasms: Results of a Phase 1 Clinical Trial," Lasers in Surgery and Medicine, vol. 42., pp. 728-735 (2010).

DC Shackley, et al., "Photodynamic therapy," Journal of Royal Society of Medicine, vol. 92, pp. 562-565, Nov. 1999.

* cited by examiner

PHOTODYNAMIC THERAPY INCLUDING LIGHT PRETREATMENT

CROSS REFERENCE TO RELATED APPLICATIONS

This application claims priority to, and any other benefit of U.S. Provisional Application No. 61/383,390, filed on Sep. 16, 2010 and entitled "Photodynamic Therapy Including Light Pretreatment," and U.S. Provisional Application No. 61/383,365, filed on Sep. 16, 2010 and entitled "Flexible Photodynamic Therapy Device and Method for Large Heterogeneous Lesions," both of which are hereby incorporated by reference in their entirety.

BACKGROUND OF THE INVENTION

Photodynamic therapy, also referred to herein as "PDT", is a process for treating various types of disease such as psoriasis and cancer wherein light irradiation is used to activate a photosensitizing agent which then attacks the target tissue through one or more photochemical reactions, thereby producing a cell-killing, or cytotoxic, effect. It has been discovered that when certain photosensitizer compounds are applied to the human or animal body, they are selectively retained by diseased (e.g., psoriatic or cancerous) tissue while being eliminated by healthy tissue. The diseased tissue containing the photosensitizer can then be exposed to therapeutic light of an appropriate wavelength and at a specific intensity for activation. The light energy, oxygen, and the photosensitizer cause a photochemical reaction which kills the cells in which the photosensitizer resides.

Phthalocyanines represent a known class of photosensitizing agents. The silicon phthalocyanine Pc 4 is currently in early clinical trials for dermatologic conditions, and has demonstrated an excellent safety profile when used topically on skin lesions. The conventional procedure for administration of Pc 4 is application to skin, followed by activation using 675 (+/−5) nm red light after one hour. The interaction of Pc 4, red light, and molecular oxygen in the tissue results in a photodynamic effect, characterized by oxidative stress leading to apoptosis of pathologically relevant cells.

One of the current limitations of topical Pc 4 PDT is the limited cutaneous penetration of Pc 4 formulations. Confocal imaging studies of human skin 1-2 hours after Pc 4 had been applied showed significant absorption in the epidermis, but minimal to no absorption in the papillary dermis. Both the epidermis and the papillary dermis contain immunologic and other cells that it would be preferable to be able to reach in order to effectively treat certain cutaneous pathologies with PDT. Accordingly, a method for providing the delivery of photosensitizer agents such as Pc 4 to deeper tissue levels is needed.

SUMMARY OF THE INVENTION

The present invention provides a method for improving the penetration of tissue by photosensitizer agents such as phthalocyanines. Advantages provided by the invention can include penetration of the photosensitizer to a greater depth and/or more rapid penetration of tissue by the photosensitizer.

In one aspect, the present invention provides a method of photodynamic therapy that includes administering a therapeutically effective amount of a photosensitizer to an area of tissue of a subject, delivering a first photoirradiation by light having a wavelength suitable to activate the photosensitizer to the area of tissue, allowing a sufficient interval of time to pass for an effective amount of the photosensitizer to substantially penetrate the tissue, and then delivering a second photoirradiation by light having a wavelength suitable to activate the photosensitizer to provide a therapeutic effect. In particular embodiments, the tissue to which the photodynamic therapy is applied is skin.

BRIEF DESCRIPTION OF THE DRAWINGS

FIG. 2 includes 4 sets of images obtained from confocal imaging of skin sections from two psoriasis patients with lesions to which Pc 4 (0.1 mg/ml) versus Pc 4 (0.1 mg/ml) plus 100 J/cm2 of red light (675 nm) was applied.

DETAILED DESCRIPTION OF THE INVENTION

Figure 1:
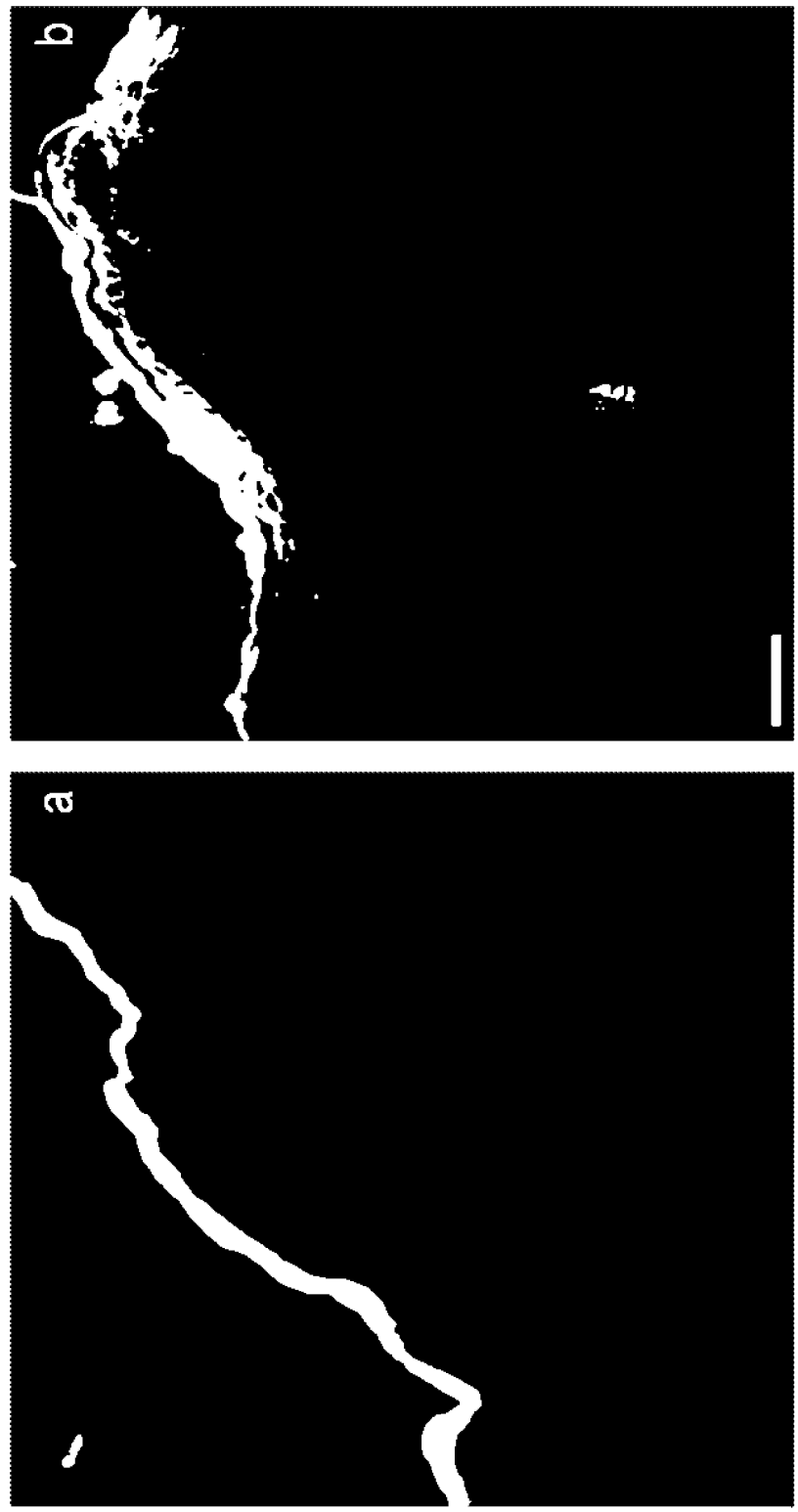
FIG. 1 is a pair of photographs showing that photoirradiation of mouse ear skin to which Pc 4 had been topically applied facilitates Pc 4 penetration into the skin. Part (a) shows Pc 4 (0.1 mg/mL) fluorescence after 15 minutes of topical application on mouse ear skin. Part (b) shows that the depth of Pc 4 (0.1 mg/mL) is enhanced by an initial, small dose (50 J/cm2) of light energy delivered to the mouse ear skin; Scale bar, 50 uM.
Figure 2A:
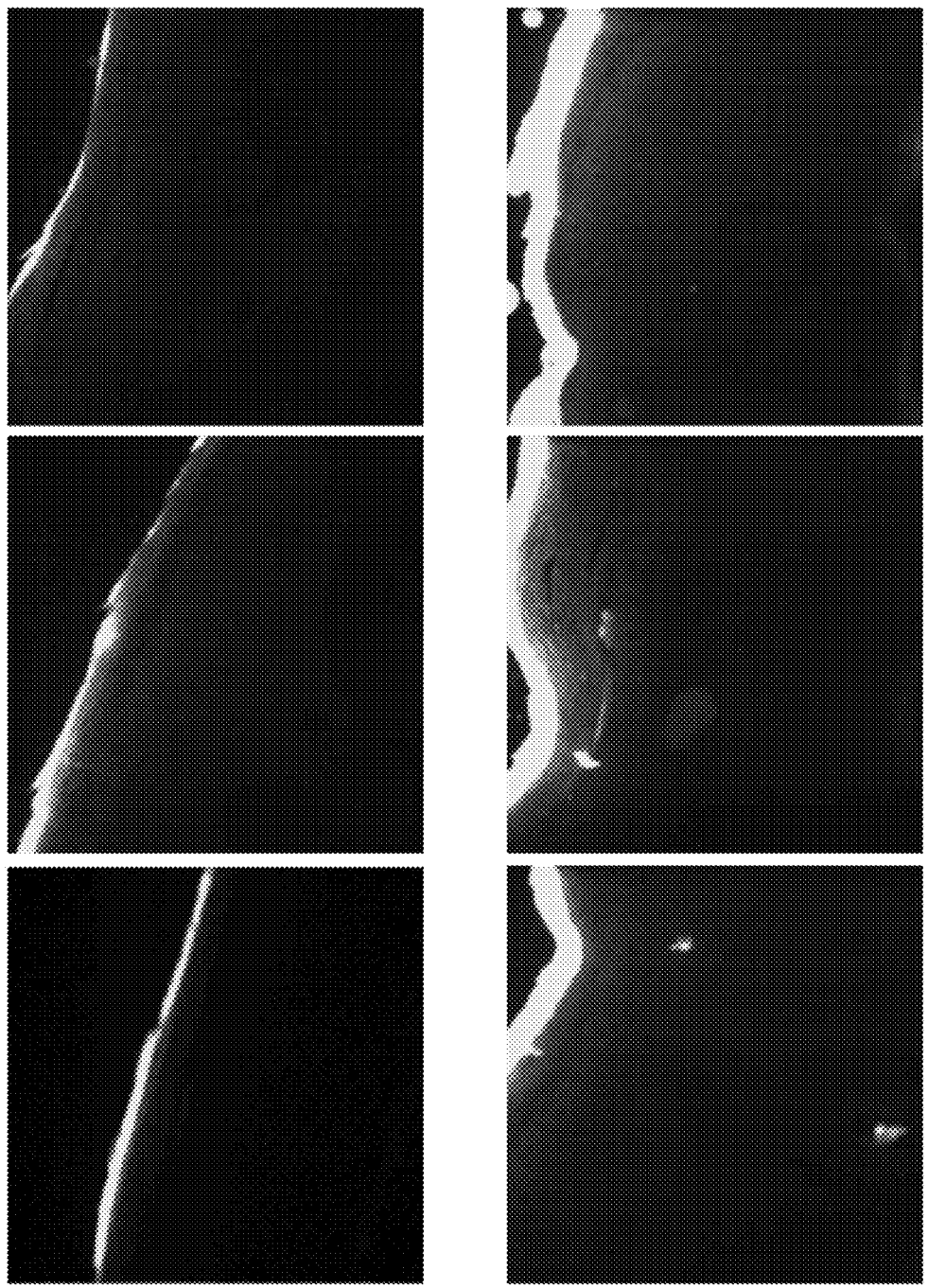
FIG. 2a, top panels (Pc 4 alone), shows Pc 4 fluorescence limited to the stratum corneum after more than one hour of Pc 4 application, whereas the lower panel shows Pc 4 fluorescence not only in the stratum corneum but also in the epidermis and upper dermis after 1 hour of Pc 4 followed by 100 J/cm2 of light.
Figure 2B:
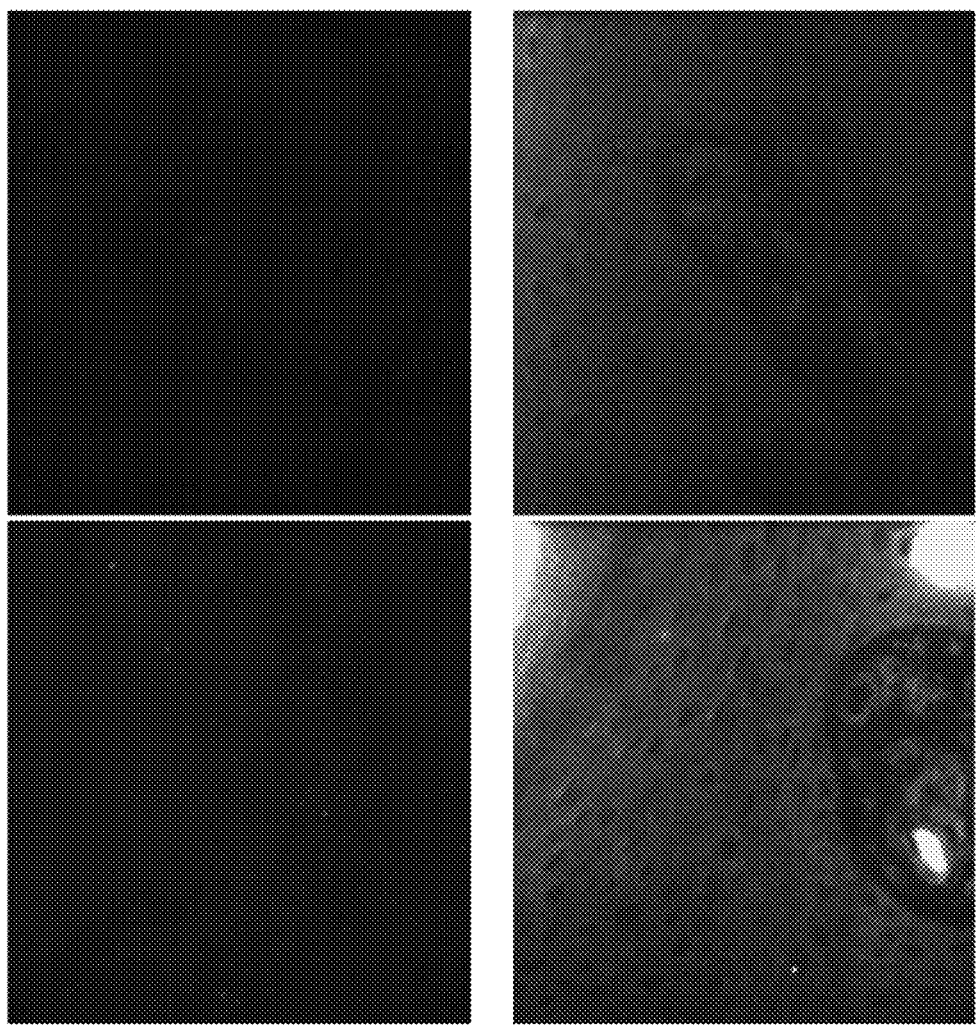
FIG. 2b is a higher magnification emphasizing that there is indeed Pc 4 fluorescence in the cells within the epidermis and upper dermis in the lower panel (i.e. Pc 4+light) which is not observed in the upper panel (i.e. Pc 4 alone).
Figure 2C:
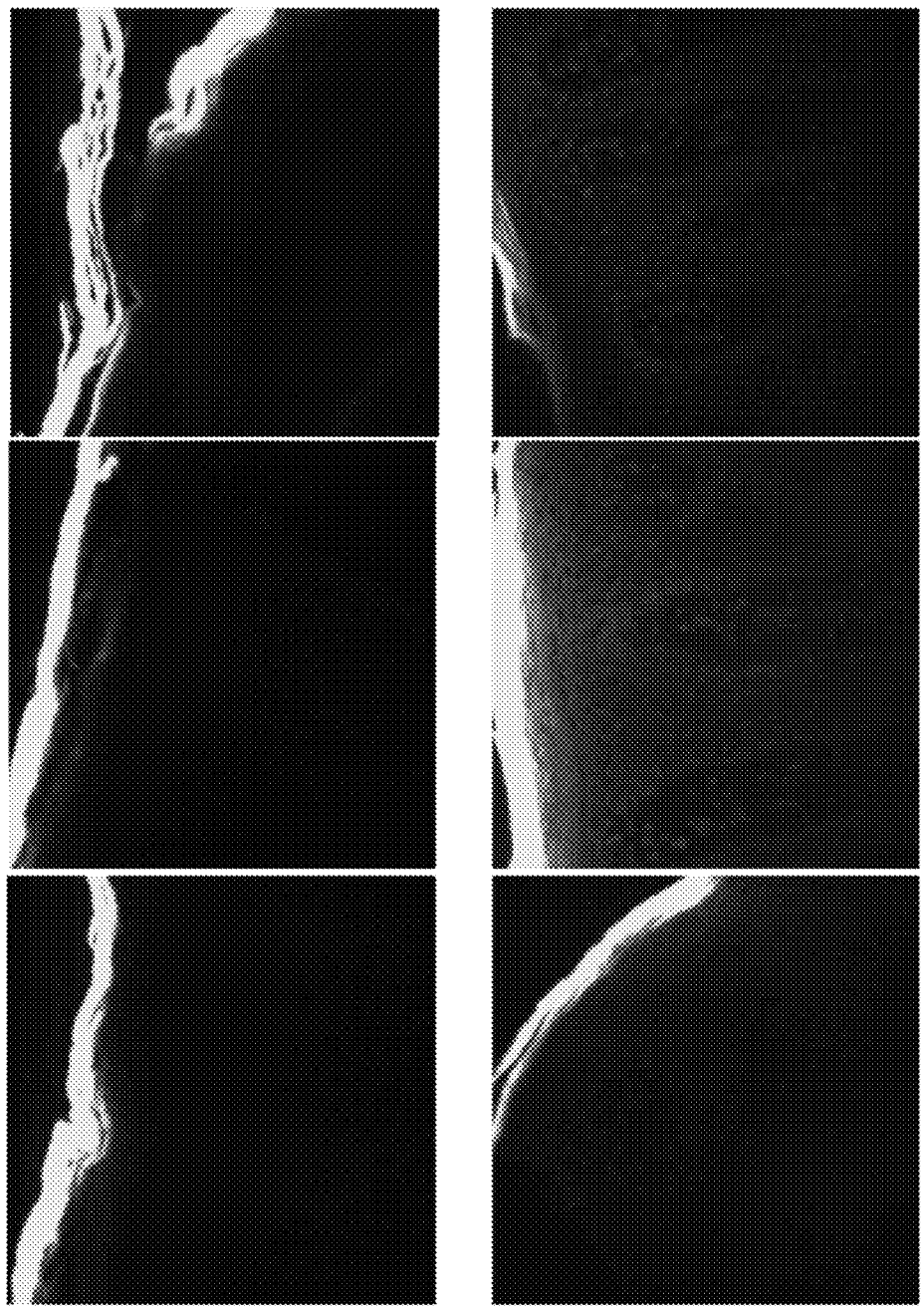
FIGS. 2c and 2d are similar images obtained from another patient, showing similar results as those provided in FIGS. 2a and 2b.
Figure 2D:
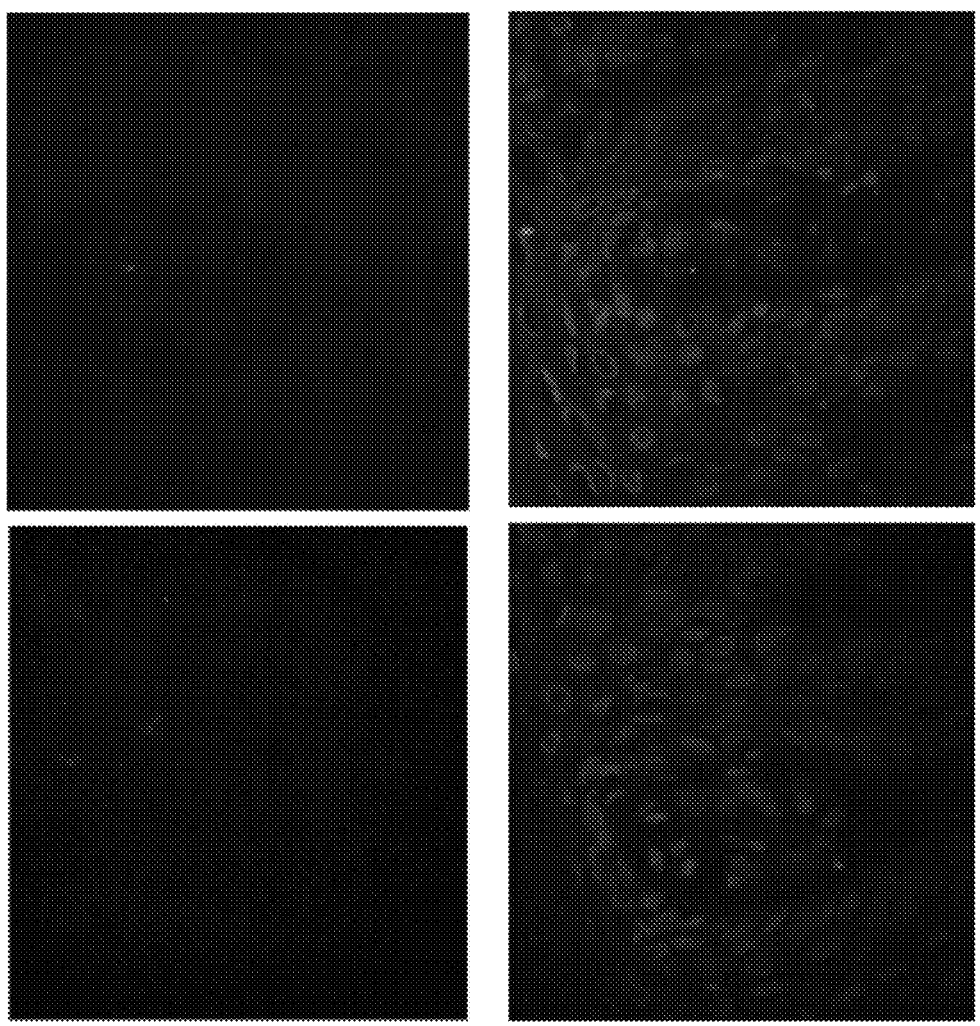

The present invention relates in part to a method of photodynamic therapy that includes activating a photosensitizer with photoirradiation after application of the photosensitizer to tissue in order to increase penetration of the tissue by the photosensitizer, and then administering a subsequent photoirradiation to activate the photosensitizer again when it has penetrated the tissue to a desired depth.

Light pretreatment can be used to increase penetration by photosensitizing agents in a variety of tissues. Examples of tissue include epithelial, mesothelial, synovial, fascial, or serosal tissue, including, but not limited to, the eye, esophagus, mucous membrane, bladder, joint, tendon, ligament, bursa, gastrointestinal, genitourinary, pleural, pericardial, pulmonary, or uroepithelial tissue. In a preferred embodiment, the tissue being treated is skin. As used herein, skin refers to the multilayer organ including the epidermis, dermis, and hypodelinis (i.e., subcutaneous tissue) that covers the majority of the surface of mammalian subjects such as human beings, and also includes mucous membranes that are contiguous with the outer skin. While the description herein primarily refers to use of photodynamic therapy including light pretreatment to treat skin, it should be understood that the methods can be used to increase penetration of photosensitizing agents through other tissue.

The first step of the method includes administering a therapeutically effective amount of a photosensitizer to an area of tissue of a subject. This method can be used with a wide variety of different photosensitizers known to those skilled in the art. Photosensitizers are agents that absorb light of a particular wavelength and transfer this energy to oxygen molecules to form highly reactive oxygen species that provide a therapeutic effect. Examples of photosensitizers known to those skilled in the art include phthalocyanines porphyrins, porphyrin precursors, porphycenes, naphthalocyanines, phenoselenazinium, hypocrellins, perylenequinones, texaphyrins, benzoporphyrin derivatives, azaporphyrins, purpurins, Rose Bengal, xanthenes, porphycyanines, isomeric porphyrins, pentaphyrins, sapphyrins, chlorins, benzochlorins, hypericins, anthraquinones, rhodanols, barbituric acid derivatives, expanded porphyrins, dipyrromethenes, coumarins, azo dyes, acridines, rhodamine, azine derivatives, tetrazolium derivatives, safranines, indocyanines, indigo derivatives, indigo triazine derivatives, pyropheophorbides, pyrrole derived macrocyclic compounds, naturally occurring or synthetic porphyrins, naturally occurring or synthetic chlorins, naturally occurring or synthetic bacteriochlorins, naturally occurring or synthetic isobacteriochlorins, naphthalocyanines, phenoxazine derivatives, phenothiazine derivatives, chalcoorganapyryllium derivatives, triarylmethane derivatives, rhodamine derivatives, fluorescein derivatives, verdin derivatives, toluidine blue derivatives, methylene blue derivatives, methylene violet derivatives, nile blue derivatives, nile red derivatives, phenazine derivatives, pinacyanol derivatives, plasmocorinth derivatives and indigo derivatives, and combinations thereof.

Photosensitizer compounds known by those skilled in the art to be particularly suitable for photodynamic therapy include porphyrins such as Photofrin®, benzoporphyrins such as Verteporfin®, chlorins such as Foscan®, purpurins such as Purlytin®, texaphyrins such as LuTex®, pheophorbides such as HPPH, and phthalocyanines such as Photosense or Pc 4. Also included herein is the use of photosensitizer precursors such as 5-aminolaevulinic acid, which is converted to protoporphyrin IX by cells upon delivery. A preferred group of photosensitizers are phthalocyanines, such as Pc 4. Pc 4 is preferred in part because of its higher molar extinction coefficient and its peak absorption wavelength, which facilitates deep tissue penetration by the light, and its chemical purity. See Baron et al., Lasers in Surgery and Medicine 42, 728-735 (2010), the disclosure of which is incorporated herein by reference.

The area of tissue to which the photosensitizer is applied can vary depending on the nature of the disease or condition be treated or prevented. Typically, treatment is confined to the area in which the disease or abnormal condition is exhibited, or where the disease or condition is expected to occur in the case of prophylactic treatment. A preferred tissue for treatment is the skin. Areas of skin that can be treated include portions of skin on the head, arms, legs, and torso. In some embodiments, the skin area includes all of the skin exhibiting the skin disease or abnormal skin condition, whereas in other embodiments the skin area treated at a particular time includes only a portion of the skin exhibiting the skin disease or abnormal skin condition.

The photosensitizer can be administered to the area of tissue immediately before the first photoirradiation is delivered, or the first photoirradiation can be delayed to provide some time for the photosensitizer to be taken up by the upper tissue layer. For example, the first photoirradiation can be administered from 0.5 to 5 minutes after administration of the photosensitizer to the tissue. The photosensitizer can be administered in pure form, applied after being dissolved in a non-toxic solvent, or it can be administered in a topical formulation. The solution including the photosensitizer can be administered to the area of tissue by a suitable device such as a syringe or pipette, and can then be manually spread over the area of tissue (e.g., by a gloved finger). Alternately, the photosensitizer solution can be applied to an area of tissue via a spray.

The method of the invention includes administering a first photoirradiation with light having a wavelength suitable to activate the photosensitizer to the area of tissue. A second photoirradiation is subsequently administered in a later step. A photoirradiation, as used herein, refers to shining light for a discrete period of time, typically only a few seconds or minutes. The light should be administered for a period of time and intensity sufficient to activate the photosensitizing agent. For a phthalocyanine compound, 10 to 20 J/cm$^2$ of energy will typically be sufficient to activate the compound. However, amounts ranging from about 5 to about 200 J/cm$^2$ can be used in some embodiments of the invention.

The amount of light applied in the first and subsequent photoirradiation can be the same or they can be different. Preferably, the total energy provided by the combined photoirradiation is from about 50 to about 200 J/cm$^2$. The light can be provided by a laser, light emitting diode, or other light source known to those skilled in the art. The light can be provided by a single source, or a plurality of light sources can be used. In the case of internal tissue, it is necessary to either provide access to the tissue for the light source, or to provide an arthroscopic light source. For example, the tissue can first be exposed through surgery, or the light can be delivered through an optical cable.

The light can also be administered by a device worn by a subject that positions the light source or sources over the area of skin to be treated. An example of a device suitable for being positioned on a subject is a device including a flexible panel having a plurality of light sources distributed across a conformable light delivery surface thereof. The plurality of light sources can be configured to provide a treatment light to achieve a desired therapeutic effect at a predetermined distance from the light delivery surface. The device can also be provided with spacers configured at the light delivery surface to position the light delivery surface at the predetermined distance from a treatment area of a subject. Such devices are further described in U.S. patent application Ser. No. 13/824,274, entitled "Photodynamic Therapy System, Device and Associated Method of Treatment," the disclosure of which is incorporated herein by reference.

The light delivered to the area of tissue should have a wavelength or wavelengths suitable for activating the photosensitizer. The wavelength is typically within the wavelengths of visible and near infra-red light, which includes wavelengths from about 420 nm to about 780 nm. However, specific photosensitizers typically respond to light having a particular wavelength. For example, phthalocyanine-based photosensitizers generally respond to light within the range of about 650 nm to about 700 nm, with the suitable wavelength for activation of the phthalocyanine Pc 4 being about 675 nm. While it is preferable that the light being delivered consist primarily of light having the desired wavelength, other wavelengths of light can be present in the light delivered.

Once the first photoirradiation has been delivered to the area of tissue, a sufficient interval of time should be allowed to pass for an effective amount of the photosensitizer to further penetrate the tissue. In the case of skin tissue, a sufficient interval of time is preferably provided to allow the photosensitizer to reach the lower levels of skin such as the basal epidermis and/or the papillary dermis, which is the upper layer of the dermis immediately beneath the epidermis. The particular layer of skin targeted can vary depending on the disease being treated. Examples of sufficient intervals include 1 hour, 30 minutes, 10 minutes, 5 minutes, or any other interval within this range. In addition to providing sufficient time for the photosensitizer to penetrate the skin to the desired level, care should also be taken to avoid providing too much time, which can result in passage of significant amounts of the photosensitizer beyond the intended site. For Pc 4, the time interval needed for delivery through skin is typically only fifteen minutes or less, which is significantly less than the hour or more that is required for phthalocyanine penetration to lower skin levels in the absence of a first photoirradiation.

When treating skin, the area of skin can be covered with an opaque dressing during the interval of time between the first and second photoirradiation to prevent further activation of the photosensitizer by ambient light. While not intending to be bound by theory, the first photoirradiation may increase the ability of the photosensitizing agent to penetrate tissue as a result of breaking up aggregates of the photosensitizing agent and/or by disrupting the tissue barrier as a result of the release of reactive oxygen species. Accordingly, this first photoirradiation can also be referred to as the disruptive photoirradiation, or light pretreatment. The ability of light pretreatment to facilitate the penetration of photosensitizer to lower levels of skin is illustrated by FIGS. 1 and 2. In particular, FIG. 2 indicates that an initial dose of light on psoriatic lesions in humans to which Pc 4 has been applied facilitates the absorption of Pc 4 into the epidermis and upper dermis.

An effective amount of the photosensitizer is an amount of photosensitizer sufficient to provide the desired therapeutic effect. Since the therapeutically effective amount is the amount of photosensitizer that must be administered to the skin, and the effective amount is the amount the provides an actual photodynamic effect at the desired level within the tissue, the effective amount will typically be somewhat less than the therapeutic amount, based in part on how well the photosensitizer penetrates the tissue. While not intending to be bound by theory, it is believed that the target cells of many skin diseases and conditions are present in lower levels of the skin, and therefore it is preferable to increase the depth and/or speed of penetration of the skin by the photosensitizing agent.

A variety of methods are available to determine the amount of energy and/or time necessary for an effective amount of the photosensitizer to reach the desired tissue level, such as a lower level of the skin, under the conditions being used. Such methods can be referred to as photosensitizer localization assays. For example, a biopsy can be obtained after administration of the photosensitizer from which the photosensitizer is chemically extracted and quantified using conventional analytic techniques such as UV spectrophotometry. The photosensitizer (e.g., Pc 4) can also be identified from biopsy samples using confocal imaging of the fluorescence of the photosensitizer either with or without the use of additional labels targeted at specific intracellular components (e.g., DAPI, mitotracker). Such techniques can be helpful to determine therapeutically effective doses, and also to evaluate non-responding subjects for possible poor photosensitizer permeation through the skin or other complications.

Another photosensitizer localization assay is based on the detection of reactive oxygen species generated by the photosensitizer. This type of assay includes the steps of obtaining a tissue biopsy sample from the treated tissue area, adding a compound such as 2',7'-dichlorofluorescein (DCF) that reacts with oxygen radicals to produce a signal, shining a light having an appropriate wavelength to activate the photosensitizer agent (e.g., about 675 nm light for Pc 4), and observing the tissue using a confocal microscope. The amount of photosensitizer present at the desired skin level can readily be determined using the confocal microscope, as it will create oxygen radicals upon light activation which will be detected by the oxygen radical detector compound (e.g., DCF) which produces a proportional signal. This can be used to determine whether or not an effective amount of the compound is present. This method has the advantage of assuring that the photosensitizer that has reached the desired tissue level is not only present at a desired concentration, but that the photosensitizer has retained activity upon reaching the desired tissue level.

Alternately, to determine if an effective amount of photosensitizer is being delivered, changes in the tissue area being treated can be evaluated. For example, the histology of the tissue can be evaluated using stains such as hematoxylin and eosin and evaluating using a conventional or electron microscope. Protein expression levels known to reflect PDT outcomes can also be used. Protein levels can be measured by techniques such as immunohistochemistry or Western blot analysis. Examples of suitable proteins for histological evaluation of skin tissue include HIF1, caspase, MMP, and Bcl-2.

The amount of light energy necessary to obtain effective results during photoirradiation (e.g., a first or second photoirradiation) can be pre-determined by evaluating the effective amounts for particular subjects, types of subjects, photosensitizers, and/or formulations. The amount of light energy can also be regulated in response to feedback during treatment. For example, the amount of light being delivered can be regulated based on concurrent analysis of photosensitizer penetration, heat level in the tissue (e.g., skin), or the level of discomfort being experienced by the subject.

After a sufficient interval of time has passed since the first photoirradiation, a subsequent photoirradiation with light having a wavelength suitable to activate the photosensitizer is delivered to the area of tissue (e.g., skin) to provide a therapeutic effect. The amount of energy delivered during this second photoirradiation ranges from about 5 to about 200 J/cm$^2$. This subsequent photoirradiation may be referred to as the therapeutic photoirradiation. The wavelength of light used in subsequent photoirradiation should be substantially the same as that used for the first photoirradiation in order to activate the photosensitizing agent (e.g., stimulate formation of reactive oxygen species). However, the amount of energy delivered by the therapeutic photoirradiation is greater than the amount of energy delivered in the first photoirradiation in many embodiments, since the intensity of the light typically decreases as it passes through layers of tissue. Nonetheless, the subsequent photoirradiation step can also provide an equal or lower amount of energy to the area of tissue relative to the first photoirradiation in other embodiments. For example, using a constant energy and light wavelength, one can administer a first photoirradiation for about 1 to 15 minutes or from 5 to 10 minutes, and a second photoirradiation for about 1 to 30 minutes or from about 10 to 20 minutes. The subsequent photoirradiation can be administered by the same types of devices suitable for administering the first photoirradiation.

The main difference in effect for the subsequent photoirradiation is that while the first photoirradiation releases reactive oxygen in the upper levels of tissue (i.e., the epidermis when the tissue is skin), the subsequent photoirradiation releases reactive oxygen species in relatively lower or deeper tissue levels. For skin treatment, the lower tissue level can be the basal layer of the epidermis, where most epithelial skin cancers arise, or the papillary dermis, where most of the T lymphocytes involved in the immune-mediated disease psoriasis reside. The difference in effect results from the movement of the photosensitizer to the lower skin levels as a result of movement through the tissue during the interval of time. In addition, while the purpose of the first photoirradiation is to facilitate transport of the photosensitizer through the tissue, the purpose of the subsequent photoirradiation is to activate the photosensitizing agent to provide a therapeutic effect.

In further embodiments of the invention, one or more additional photoirradiations are administered to the area of tissue (e.g., skin) being treated. The additional photoirradiations can be disruptive photoirradiations, they can be therapeutic photoirradiations, or they can provide a combined effect. For example, one, two, three, or more additional disruptive and/or therapeutic photoirradiations can be used. However, an excessive exposure to light (e.g., continuous exposure) is undesirable as this may accelerate photobleaching of the photosensitizer and rapidly exhaust its ability to generate reactive oxygen species, thereby reducing the therapeutic effect at lower levels of the tissue. In addition, excessive exposure can also increase discomfort by the subject receiving treatment. When additional photoirradiations are administered, it may also be preferable to escalate the amount of energy being delivered during each subsequent period. For example, three photoirradiations can by administered using first 50, then 75, and finally 100 J/cm² of light of an appropriate wavelength.

Additional means known to those skilled in the art for increasing penetration of the photosensitizer into the lower levels of tissue (e.g., skin) can also be used together with the light pretreatment method described herein. These additional means include the delivery of electric current, ultrasound, radio energy, microneedles, iontophoresis, and sonophoresis to the area of skin being treated. The additional means can be used any time during the method, such as before the first photoirradiation, during the first photoirradiation, during the interval between the first and second photoirradiation, during the second photoirradiation, or any combination thereof.

The method can be used to treat or prevent a variety of different diseases and abnormal conditions in a subject. In particular, the method can be used to treat a skin diseases and abnormal conditions. For example, the method can be used to treat or prevent skin disease such as skin cancer. Photodynamic therapy using light pretreatment can also be used to treat or prevent other types of skin disease such as fungal, microbial, or viral skin infections. Non-infective skin diseases such as psoriasis can also be treated or prevented. Examples of abnormal skin conditions that can be treated by the present invention include chronic or acute dermatitis and acne. In addition, the method can be used for cosmetic purposes, for example to improve the appearance of skin.

Cancer, as used herein, refers to a disease of abnormal and excessive cell proliferation, as known by those skilled in the art, and also includes precancerous conditions. Skin cancers include, but are not limited to nonmelanoma skin cancers such as basal cell carcinoma, squamous cell carcinoma, precancers or in situ cancers such as actinic keratoses, Bowen's disease, and T cell malignancies such as mycosis fungoides/cutaneous T-cell lymphoma.

"Treat", "treating", and "treatment", etc., as used herein, refer to any action providing a benefit to a subject afflicted with a disease or abnormal condition such as cancer or psoriasis, including improvement in the condition through lessening or suppression of at least one symptom, or delay in progression of the disease, etc. In one embodiment of treatment, administration of the compounds is effective to eliminate the cancer; in another embodiment, administration of the photosensitizer is effective to decrease the severity of the cancer or lengthen the lifespan of the subject so afflicted. Prevention or prophylaxis of disease, on the other hand, refers to either a complete avoidance or delay in the onset of a disease or condition.

Embodiments of the invention may use phthalocyanine compounds as photosensitizers. A wide variety of phthalocyanine compounds has been developed, having a variety of absorption wavelengths, solubilities, and other characteristics. See for example U.S. patent application Ser. No. 10/599,433, entitled "Topical Delivery of Phthalocyanines" and U.S. patent application Ser. No. 12/408,116, entitled "Phthalocyanine Salt Formulations," the disclosures of which are incorporated by reference herein. Metal phthalocyanines and phthalocyanines bearing axial ligands in particular have been used as photosensitizing agents as a result of their capacity for redox chemistry. Metal phthalocyanines include a diamagnetic metal ion moiety that is either coordinated or covalently bound to the phthalocyanine core. The metal ion can be selected from aluminum (Al), germanium (Ge), gallium (Ga), tin (Sn), zinc (Zn) and silicon (Si) or any other suitable diamagnetic metal ion. Phthalocyanines bearing an axial ligand include phthalocyanine compounds with modifying moieties linked to the central metal.

Representative phthalocyanine compounds include compounds generally characterized by the following formula (I), or a pharmaceutically acceptable salt thereof

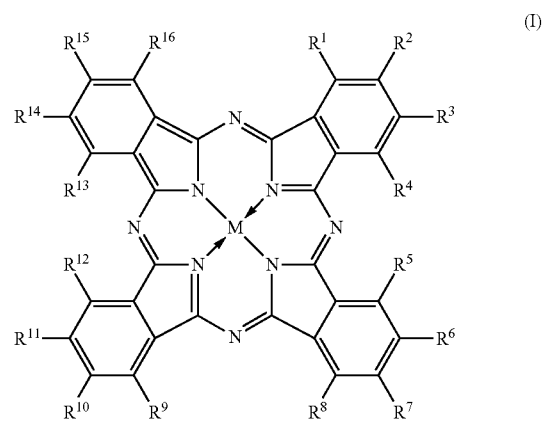

(I)

Phthalocyanine compounds include 16 points along the circumference of the fused ring structure that can be represented by $R^1$-$R^{16}$. These positions can be substituted with a wide variety of functional groups. For example, $R^1$-$R^{16}$ can each be independently selected from hydrogen, halogen, nitro, cyano, hydroxy, thiol, amino, carboxy, aryl, heteroaryl, carbocyclyl, heterocyclyl, $C_{1-20}$alkyl, $C_{1-20}$alkenyl, $C_{1-20}$alkynyl, $C_{1-20}$alkoxy, $C_{1-20}$acyl, $C_{1-20}$alkylcarbonyloxy, $C_{1-20}$aralkyl, $C_{1-20}$hetaralkyl, $C_{1-20}$-carbocyclylalkyl, $C_{1-20}$heterocyclylalkyl, $C_{1-20}$-aminoalkyl, $C_{1-20}$alkylamino, $C_{1-20}$thioalkyl, $C_{1-20}$alkylthio, $C_{1-20}$hydroxyalkyl, $C_{1-20}$alkyloxycarbonyl, $C_{1-20}$-alkylaminocarbonyl, $C_{1-20}$alkylcarbonylamino, and $C_{1-10}$alkyl-Z—$C_{1-10}$alkyl. Z is selected from S, $NR^{17}$, and O, and if present $R^{17}$ is selected from hydrogen, $C_{1-20}$acyl, $C_{1-20}$alkyl, and $C_{1-20}$aralkyl.

Additional embodiments of the invention can use phthalocyanine compounds in which the substituents along the circumference are divided into two groups. Substituents on fused ring structures can be peripheral or non-peripheral substituents. A non-peripheral substituent, as defined herein, is a substituent which is adjacent (i.e., α) to the point of fusion between an outer phenyl ring and an inner pyrrole ring, as found in phthalocyanine compounds as exemplified by Formula (I) herein. A substituent is peripheral, on the other hand, when it is not a non-peripheral substitutent. For example, in Formula I provided herein, the substituents $R^2$, $R^3$, $R^6$, $R^7$, $R^{10}$, $R^{11}$, $R^{14}$, and $R^{15}$ are peripheral substituents.

In this addition embodiment, $R^1$, $R^4$, $R^5$, $R^8$, $R^9$, $R^{12}$, $R^{13}$, and $R^{16}$ are each independently selected from hydrogen, halogen, nitro, cyano, hydroxy, thiol, amino, and methyl; and $R^2$, $R^3$, $R^6$, $R^7$, $R^{10}$, $R^{11}$, $R^{14}$, and $R^{15}$ are each independently selected from hydrogen, halogen, nitro, cyano, hydroxy, thiol, amino, carboxy, aryl, heteroaryl, carbocyclyl, heterocyclyl, $C_{1-6}$alkyl, $C_{1-6}$alkenyl, $C_{1-6}$alkynyl, $C_{1-6}$alkoxy, $C_{1-6}$acyl, $C_{1-6}$alkylcarbonyloxy, $C_{1-6}$-carbocyclylalkyl, $C_{1-6}$-aminoalkyl, $C_{1-6}$alkylamino, $C_{1-6}$thioalkyl, $C_{1-6}$alkylthio, $C_{1-6}$hydroxyalkyl, $C_{1-6}$alkyloxycarbonyl, $C_{1-6}$alkylaminocarbonyl, and $C_{1-6}$alkylcarbonylamino.

Within the center of the fused ring structure of the phthalocyanine compound of formula I is M. M is a diamagnetic metal ion optionally complexed with or covalently bound to one or two axial ligands, wherein the metal ion is coordinated to the phthalocyanine moiety.

In a number of embodiments, the axial ligand M is $(G)_a Y[OSi(CH_3)_2(CH_2)_b N_c(R')_d(R'')_e)_f X d_g]_p$; wherein Y is selected from Si, Al, Ga, Ge, Zn, or Sn;

R' is selected from H, $CH_3$, $C_2H_5$, $C_4H_9$, $C_4H_8NH$, $C_4H_8N$, $C_4H_8NCH_3$, $C_4H_8S$, $C_4H_8O$, $C_4H_8Se$, $OC(O)CH_3$, $OC(O)$, CS, CO, CSe, OH, $C_4H_8N(CH_2)_3CH_3$, $(CH_2)_2N(CH_3)_2$, $(CH_2)_nN((CH_2)_o(CH_3))_2$, and an alkyl group having from 1 to 12 carbon atoms;

R'' is selected from H, $SO_2CH_3$, $(CH_2)_2N(CH_3)_2$, $(CH_2)_{11}CH_3$, $C(S)NHC_6H_{11}O_5$, $(CH_2)_nN((CH_2)_o(CH_3))_2$, and an alkyl group having from 1 to 12 carbon atoms;

G is selected from OH and $CH_3$;

a is 0 or 1; b is an integer from 2 to 12; c is 0 or 1; d is an integer from 0 to 3; e is an integer from 0 to 2; f is 1 or 2; g is 0 or 1; n is an integer from 1 to 12; o is an integer from 1 to 11; and p is 1 or 2.

A preferred phthalocyanine is "Pc 4", which is a compound having a structure of Formula (I), wherein M is HOSiPcOSi$(CH_3)_2(CH_2)_3N(CH_3)_2$.

In salt forms of the compound, X of formula I can be selected from a pharmaceutically acceptable anion and the adjacent amine will be a quaternary amine having a positive charge. Together the anion and quaternary amine form the salt. The salts chosen for this work can be selected from those formed by acids giving physiologically ubiquitous ions or intermediate metabolite ions in biochemical pathways, such as the acids designated as Class 1 by Stahl (Handbook of Pharmaceutical Salts; Stahl, P. H.; Wermuth, C. G. Eds; Wiley-CH: New York, 2002; p 9-18), or those formed by acids showing little toxicity and good tolerability.

In some embodiments of the invention, the photosensitizer includes a free base (e.g., an amine site) and which reacts with an acid to form a salt. Thus, suitable pharmaceutically acceptable salts of photosensitizers may be prepared from an inorganic acid or from an organic acid. Examples of such inorganic acids are hydrochloric, hydrobromic, hydrofluoric, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, siloxane, β-hydroxybutyric, galactaric, and galacturonic acids. In the case of phthalocyanine photosensitizers, the acid forms a counterion upon associating with amines of the phthalocyanine. Examples of preferred counter ions include chloride, bromide, nitrate, sulfate, tosylate, phosphate, tartrate, and maleate. Another set of suitable counter ions includes malate, mesylate, inosate, dimethylphosphonate, methylsulfonate, and sulfonate anions.

The photosensitizer is preferably applied as part of a topical formulation. Topical administration of the photosensitizer can be accomplished using various different formulations such as powders, sprays, ointments, pastes, creams, lotions, gels, solutions, or patches. The photosensitizer may be mixed under sterile conditions with a pharmaceutically acceptable carrier, and with any preservatives, buffers, or propellants which may be required. The ointments, pastes, creams, solutions, foams, lacquers, oils and gels may contain excipients in addition to the photosensitizer active ingredient. An example of a suitable formulation for topical delivery of a photosensitizer is a 70% ethanol and 30% propylene glycol solution.

Examples of topical formulations include ointments and creams. Ointments are homogeneous, semi-solid preparations intended for external application to the skin or mucous membranes. They are used as emollients or for the application of active ingredients to the skin for protective, therapeutic, or prophylactic purposes and where a degree of occlusion is desired. Ointments can be formulated using hydrophobic, hydrophilic, or water-emulsifying bases to provide preparations for various applications. Creams, on the other hand, are semi-solid emulsions; i.e., a mixture of oil and water. They are divided into two types: oil-in-water creams which are composed of small droplets of oil dispersed in a continuous aqueous phase, and water-in-oil creams which are composed of small droplets of water dispersed in a continuous oily phase.

The dosage amount and preferred type of formulation can be readily established by reference to known treatment or prevention regimens. The amount of photosensitizer that is administered and the dosage regimen for treating a disease condition with a photosensitizer using the method of this invention depends on a variety of factors, including the age, weight, sex, and medical condition of the subject, the severity of the disease, the site and frequency of administration, the character of the skin to which the agent is applied, and the particular compound employed, and thus may vary widely. Such treatments may be administered as often as necessary and for the period of time judged necessary by the treating physician. One of skill in the art will appreciate that the dosage regime or therapeutically effective amount of the inhibitor to be administrated may need to be optimized for each individual. The topical formulations may contain active ingredient in the range of about 0.001 to 10 mg/ml, preferably in the range of about 0.001 to 1 mg/ml and most preferably between about 0.01 and 0.1 mg/ml. Suitable amounts vary depending on the photosensitizer being used, but can be readily determined by one skilled in the art.

DEFINITIONS

Unless otherwise specified, "a," "an," "the," and "at least one" are used interchangeably and mean one or more than one. Also herein, the recitations of numerical ranges by endpoints include all numbers subsumed within that range (e.g., 1 to 5 includes 1, 1.5, 2, 2.75, 3, 3.80, 4, 5, etc.).

The term "subject" for purposes of treatment includes any human or animal subject who has a disease or condition amenable to treatment with a photosensitizing agent. For methods of prevention the subject is any human or animal subject, and preferably is a human subject who is at risk of developing a disease or condition such as cancer or psoriasis. The subject may be at risk due to exposure to carcinogenic agents, being genetically predisposed to the disease or conditions, and so on. Besides being useful for human treatment, the compounds of the present invention are also useful for veterinary treatment of mammals, including companion animals and farm animals, such as, but not limited to dogs, cats, horses, cows, sheep, and pigs. However, in most embodiments, the subject is a human subject.

A "therapeutically effective amount" of a photosensitizing compound for the method of treatment refers to an amount of the compound(s) in a preparation which, when administered as part of a desired dosage regimen, alleviates a symptom, ameliorates a condition, or slows the onset of disease conditions according to clinically acceptable standards for the disease or condition to be treated or the cosmetic purpose, e.g., at a reasonable benefit/risk ratio applicable to any medical treatment.

The term "$C_{x-y}$acyl" refers to a group represented by the general formula:

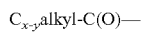

$C_{x-y}$alkyl-C(O)—

The term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively. When such alkenyl or alkynyl groups include more than one unsaturated bond, they can be referred to as polyunsaturated alkenyl or alkynyl groups.

The term "alkoxy" refers to an alkyl group having an oxygen attached thereto. Representative alkoxy groups include methoxy, ethoxy, propoxy, tert-butoxy and the like. An "ether" is two hydrocarbon groups covalently linked by an oxygen. Accordingly, the substituent of an alkyl that renders that alkyl an ether is or resembles an alkoxy.

The terms "amine" and "amino" are art-recognized and refer to both unsubstituted and substituted amines and salts thereof.

The term "aryl" as used herein includes 5-, 6-, and 7-membered substituted or unsubstituted single-ring aromatic groups in which each atom of the ring is carbon. Aryl groups include benzene, phenol, aniline, and the like.

The terms "carbocycle" and "carbocyclyl", as used herein, refer to a non-aromatic substituted or unsubstituted ring in which each atom of the ring is carbon.

The terms "heteroaryl" includes substituted or unsubstituted aromatic 5- to 7-membered ring structures, more preferably 5- to 6-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine and pyrimidine, and the like.

The term "heteroatom" as used herein means an atom of any element other than carbon or hydrogen. Preferred heteroatoms are nitrogen, oxygen, phosphorus, and sulfur.

The terms "heterocyclyl" or "heterocyclic group" refer to substituted or unsubstituted non-aromatic 3- to 10-membered ring structures, more preferably 3- to 7-membered rings, whose ring structures include one to four heteroatoms.

The term "substituted" refers to moieties having substituents replacing a hydrogen on one or more carbons of the framework. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of photodynamic therapy comprising administering a therapeutically effective amount of a photosensitizer to an area of tissue of a subject, delivering a first photoirradiation with light having a wavelength suitable to activate the photosensitizer to the area of tissue, allowing an interval of time from 5 minutes to 1 hour without photoirradiation to pass for an effective amount of the photosensitizer to substantially penetrate the tissue, and then delivering a second photoirradiation with light having a wavelength suitable to activate the photosensitizer to provide a therapeutic effect.

2. The method of claim 1, wherein the tissue is skin.

3. The method of claim 2, wherein the photosensitizer penetrates the skin sufficiently to reach the basal epidermis or the papillary dermis.

4. The method of claim 3, further comprising determining the amount of time necessary for the photosensitizer to reach the basal epidermis or the papillary dermis of the subject under the treatment conditions being used.

5. The method of claim 2, wherein the subject has a skin disease.

6. The method of claim 5, wherein the skin disease is skin cancer.

7. The method of claim 5, wherein the skin disease is psoriasis.

8. The method of claim 2, wherein the subject has an abnormal skin condition.

9. The method of claim 2, wherein the photosensitizer is administered in a topical formulation.

10. The method of claim 2, wherein the first and second photoirradiation are delivered by a device that is worn by the subject positioned over the area of skin being treated.

11. The method of claim 1, wherein the photosensitizer is a phthalocyanine compound.

12. The method of claim 11, wherein the photosensitizer is Pc 4.

13. The method of claim 11, wherein the light has a wavelength from about 650 nm to about 700 nm.

14. The method of claim 1, wherein one or more additional photoirradiations are administered between the first and second photoirradiation.

15. The method of claim 1, wherein the second photoirradiation delivers more energy than the first photoirradiation.

16. The method of claim 1, wherein the first and second photoirradiation each deliver an amount of energy independently selected from about 5 to about 200 J/cm$^2$.

\* \* \* \* \*